United States Patent [19]

Roos et al.

[11] 4,216,158
[45] Aug. 5, 1980

[54] PROCESS FOR THE PREPARATION OF 2,6-Di-TERT.-ALKYL-4-ALKYLIDENE-2,5-CYCLOHEXADIEN-ONES

[75] Inventors: Ernst Roos, Odenthal; Erika Hugl, Leverkusen, both of Fed. Rep. of Germany

[73] Assignee: Bayer Aktiengesellschaft, Leverkusen, Fed. Rep. of Germany

[21] Appl. No.: 924,311

[22] Filed: Jul. 13, 1978

[30] Foreign Application Priority Data

Jul. 29, 1977 [DE] Fed. Rep. of Germany ....... 2734239

[51] Int. Cl.² ...................... C07C 45/16; C07C 49/62
[52] U.S. Cl. .................................. 260/396 N; 568/47
[58] Field of Search .................................... 260/396 N

[56] References Cited

U.S. PATENT DOCUMENTS

| | | | |
|---|---|---|---|
| 2,940,988 | 6/1960 | Coppinger | 260/396 N |
| 3,660,505 | 5/1972 | Starnes | 260/396 N |

*Primary Examiner*—Vivian Garner

*Attorney, Agent, or Firm*—Sprung, Felfe, Horn, Lynch & Kramer

[57] ABSTRACT

A process for preparing a 2,6-di-tert-alkyl-4-alkylidene-2,5-cyclohexadien-one which comprises contacting a bis-(3,5-di-tert.-alkyl-4-hydroxybenzyl)sulphide of the formula

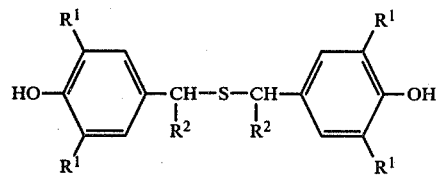

wherein
$R^1$ denotes a tertiary alkyl group and
$R^2$ denotes hydrogen, a straight or branched alkyl, cycloalkyl, cycloalkenyl, aralkyl or aryl group with lead or mercury in the oxide, hydroxide, carbonate, acetate or other basic reacting salt form at an elevated temperature in an inert solvent.

6 Claims, No Drawings

PROCESS FOR THE PREPARATION OF 2,6-DI-TERT.-ALKYL-4-ALKYLIDENE-2,5-CYCLOHEXADIEN-ONES

The invention relates to a process for the preparation of 2,6-di-tert.-alkyl-4-alkylidene-2,5-cyclohexadienones (quinone methides).

2,6-Di-tert.-alkyl-4-alkylidene-2,5-cyclohexadien-ones are known and have been prepared in a multi-stage process from 2,4,6-trialkylphenols by oxidation (U.S. Pat. No. 3923,767).

A process has been found for the preparation of 2,6-di-tert.-alkyl-4-alkylidene-2,5-cyclohexadien-ones in which a bis-(3,5-di-tert.-alkyl-4-hydroxy-benzyl) sulphide of the formula

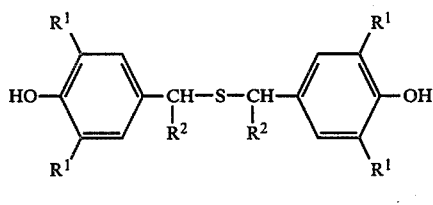

wherein
R$^1$ denotes tertiary alkyl and
R$^2$ denotes hydrogen, straight-chain or branched alkyl, cycloslkyl, cycloalkenyl, aralkyl or aryl,
is reacted with lead or mercury in the oxide, hydroxide, carbonate, acetate or other basic reacting salt form at elevated temperature in an inert solvent.

The process according to the invention can be illustrated by the following equation:

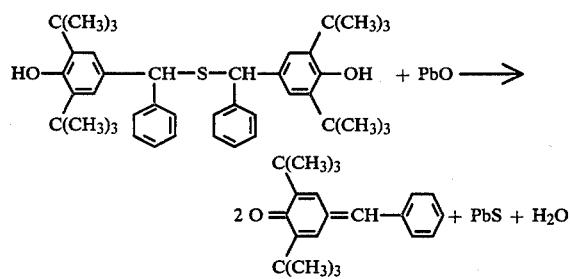

Hydrocarbon radicals which hinder the adjacent hydroxyl group may be mentioned as tertiary alkyl radicals (R$^1$) for the process according to the invention. Hydrocarbon radicals such as tert.-butyl, tert.-pentyl, tert.-hexyl, tert.-heptyl and tert.-octyl, in particular tert.-butyl, may be mentioned as preferred.

Straight-chain or branched hydrocarbon radicals with 1 to 12 carbon atoms, preferably with 1 to 6 carbon atoms, may be mentioned as alkyl (R$^2$). The following radicals may be mentioned as examples: methyl, ethyl, propyl, isopropyl, butyl, isobutyl, tert.-butyl, pentyl, isoopentyl, hexyl, isohexyl, heptyl, isoheptyl, octyl, isooctyl, nonyl, isononyl, decyl, isodecyl, dodecyl and isododecyl.

Possible cycloalkyl (R$^2$) are, in particular, five-membered and six-membered hydrocarbon rings which are optionally substituted by lower alkyl. Example which may be mentioned are: cyclopentyl, cyclohexyl and methylcyclohexyl.

Possible cycloalkenyl (R$^2$) are, in particular, five-membered and six-membered unsaturated hydrocarbon rings which are optionally substituted by lower alkyl. Examples which may be mentioned are: cyclopentenyl, cyclohexenyl and methylcyclohexenyl.

The aralkyl radicals (R$^2$) can have 1 to 4 carbon atoms in their aliphatic part and their aromatic part can be a radical from the benzene series, such as phenyl, which is optionally substituted by chlorine atoms or methyl groups. Examples which may be mentioned are the benzyl radical and the benzyl radical which is optionally substituted by chlorine atoms or methyl groups.

Aryl radicals (R$^2$) can be carbocyclic radicals from the benzene series, which can be optionally substituted by halogen, lower alkyl or phenyl. Examples of halogen substituents which may be mentioned are fluorine, chlorine, bromine or iodine. Examples which may be mentioned of alkyl substituents of the aryl radicals are methyl, ethyl, isopropyl or tert.-butyl. Examples of aryl radicals which may be mentioned are optionally substituted phenyl radicals or diphenyl radicals.

The bis-(3,5-di-tert.-alkyl-4-hydroxy-benzyl)sulphides (I) are known and can be prepared by reacting phenols and aldehydes and alkali metal sulphides (DT-OS (German Published Specification) 2,363,464).

The following starting compounds (I) may be mentioned as examples: bis-[3,5-di-tert.-butyl-4-hydroxy-(α-isopropyl)-benzyl]sulphide, bis-[3,5-di-tert.-butyl-4-hydroxy-(α-tert.-butyl)-benzyl]sulphide, bis-[3,5-di-tert.-butyl-4-hydroxy-(α-cyclohexen-Δ$^3$-yl)-benzyl]sulphide, bis-[3,5-di-tert.-butyl-4-hydroxy-(α-cyclohexyl)-benzyl]sulphide, bis-[3,5-di-tert.-butyl-4-hydroxy-(α-phenyl)-benzyl]sulphide, bis-[3,5-di-tert.-butyl-4-hydroxy-(α-p-diphenyl)-benzyl]sulphide, bis[3,5-di-tert.-butyl-4-hydroxy-(α-o-chloro-phenyl)-benzyl]sulphide, bis-[3,5-di-tert.-butyl-4-hydroxy-(α-m-chloro-phenyl)-benzyl]sulphide, bis-[3,5-di-tert.-butyl-4-hydroxy-(α-p-chloro-phenyl)-benzyl]sulphide, bis-[3,5-di-tert.-butyl-4-hydroxy-(α-o,p-dichloro-phenyl)-benzyl]sulphide, bis-[3,5-di-tert.-butyl-4-hydroxy-(α-o,o-dichloro-phenyl)-benzyl]sulphide, bis-[3,5-di-tert.-butyl-4-hydroxy-(α-o-tolyl)-benzyl]sulphide, bis-[3,5-di-tert.-butyl-4-hydroxy-(α-m-tolyl)-benzyl]sulphide and bis-[3,5-di-tert.-butyl-4-hydroxy-(α-p-tolyl)-benzyl]sulphide.

The starting compounds (I) are reacted with lead or mercury in the oxide, hydroxide, carbonate, acetate or other basic reacting salt form derived from a weak inorganic or weak organic acid. Preferably used is lead in the before-mentioned form.

The following compounds may be mentioned as examples: lead-II oxide, lead-II/IV oxide (red lead), lead-II carbonate, basic lead carbonate (2PbCO$_3$.Pb(OH)$_2$=white lead), lead oxide/carbonates of the type 3PbO.5PbCO$_3$, PbO.PbCO$_3$ and 2PbO.PbCO$_3$, basic lead acetate and mercury-II oxide.

It is particularly preferable to use basic lead carbonate.

Lead and mercury in the above-mentioned form, employed according to the invention, can be used in stoichiometric amounts, relative to the bis-(3,5-di-tert.-alkyl-4-hydroxy-benzyl)sulphide. It is also possible of course to employ the lead and mercury compounds in amounts which are less than the stoichiometric amount. An excess of lead and mercury compounds of about 100 to 110 mol%, relative to the bis-(3,5-di-tert.-alkyl-4-hydroxy-benzyl)sulphide, is preferably employed.

The process according to the invention can be carried out in the temperature range from about 50° to about 200° C., preferably in the temperature range from about 100° to about 150° C.

The process according to the invention can be carried out either under normal pressure or under reduced pressure or increased pressure. Establishing a particular pressure is not critical for the process according to the invention. In order to maintain a particular reaction temperature, the reaction can appropriately be carried out under reduced pressure when high-boiling solvents are used or under increased pressure when low-boiling solvents are used. The process according to the invention is preferably carried out under normal pressure.

The process according to the invention is carried out in a solvent which is not changed under the conditions according to the invention.

The solvent can belong to the lower alcohol, the ether, e.g. dialkyl ether, the ketone, e.g. dialkyl ketone, the acid amide e.g. alkanoic acid amide or the hydrocarbon group.

Lower alcohols for the process according to the invention can have a straight-chain or branched hydrocarbon radical ($C_1$–$C_4$) especially alkanols. Examples which may be mentioned are methanol, ethanol, isopropanol or the various isomeric butanols.

Ethers for the process according to the invention can be open-chain or cyclic ethers. Examples which may be mentioned are dioxane, tetrahydrofurane, ethylene glycol monoalkyl ethers or ethylene glycol dialkyl ethers.

The ketones for the process according to the invention can carry aliphatic ($C_1$–$C_4$) e.g. alkyl or aromatic radicals (phenyl). Examples which may be mentioned are acetone, methyl ethyl ketone, diethyl ketone or acetophenone.

Acid amides for the process according to the invention can be unsubstituted on the nitrogen atom or substituted on the nitrogen atom by lower alkyl radicals, for example methyl. Examples which may be mentioned are formamide, methylformamide, dimethylformamide or dimethylacetamide.

The hydrocarbons for the process according to the invention can belong to the aliphatic or the aromatic series and can be optionally substituted by halogen, for example chlorine, or lower alkyl groups, for example methyl. Examples which may be mentioned are benzine (gasoline) fractions with 6 to 10 carbon atoms, cyclohexane, benzene, chlorobenzene, toluene or xylene.

In a preferred reaction procedure, solvents can be employed which are water-immiscible and with which azeotropic distillation of the water of reaction formed during the process is possible. This manner of carrying out the process according to the invention enables the progress and end point of the reaction to be determined with the aid of the amount of water given off. Examples of suitable solvents for this are benzene, chlorobenzene, toluene or xylene.

The process according to the invention is preferably carried out in xylene at the boiling point of the solvent.

The process according to the invention can be carried out, for example, as follows.

The bis-(3,5-di-tert.-alkyl-4-hydroxy-benzyl)sulphide employed as the starting compound, the solvent and the required amount of the lead or mercury in the above mentioned form are introduced into a reaction vessel which is equipped with a stirrer, a thermometer, a reflux condenser and, if appropriate, a water separator.

The reaction mixture is then kept at the reaction temperature for about 5 to 12 hours, whilst stirring. In a preferred procedure, when xylene is used as the solvent, the reaction mixture is heated to the boiling point of xylene until the separation of water has ended. A reaction vessel with a water separator is required for this. The inorganic constituents are then filtered off from the cooled reaction mixture and the quinone methide prepared according to the invention is isolated by customary methods. Examples of such customary methods are: evaporating off the solvent in vacuo and isolating the end product as a crystal mass or as an oil which can be distilled, or concentrating the reaction solution and crystallising the end product from the concentrated solution, or further using the reaction solution of the end product directly. The reaction and the working-up by the process according to the invention can optionally also be carried out under an inert gas, for example under nitrogen. This measure depends on the stability of the starting compound employed.

It is known that the bis-(3,5-di-tert.-alkyl-4-hydroxybenzyl)sulphides employed as the starting compounds give 2,6-di-tert.-alkyl-4-alkenyl-phenols with alkali metal hydroxides (DT-OS (German Published Specification) No. 2,363,464). It is therefore surprising that quinone methides are formed under the basic conditions according to the invention.

The quinone methides can be advantageously prepared in a simple manner in high yields and in one reaction step by the process according to the invention.

For example, quinone methides of the formula

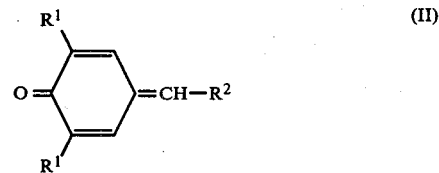

wherein

R$^1$ denotes tertiary alkyl and

R$^2$ denotes hydrogen, straight-chain or branched alkyl, cycloalkyl, cycloalkenyl, aralkyl or aryl, can be prepared by the process according to the invention.

The quinone methides can be employed as additives in the polymerization of ethylene and give rise to an improved transparency of the polyethylene prepared (U.S. Pat. No. 3,923,767).

EXAMPLE 1

Preparation of 2,6-di-tert.-butyl-4-isobutylidene-2,5-cyclohexadien-one:

277 g (0.5 mol) of bis-[3,5-di-tert.-butyl-4-hydroxy-($\alpha$-isopropyl)-benzyl] sulphide, 1,000 ml of xylene and 200 g of basic lead carbonate are heated to the boil for 5 hours using a water separator, 10 ml of water being separated off. The inorganic constituents are filtered off from the yellow xylene solution and the filtrate is evaporated to dryness in vacuo. On cooling, the residue crystallises to give a yellow crystal mass.

Yield: 251 g; corresponding to 96.5% of the theoretical yield, yellow crystals, melting point 62° to 64° C., boiling point 0.05 mbar/112° C.

EXAMPLE 2

Preparation of 2,6-di-tert.-butyl-4-cyclohexen-$\Delta^3$-yl-methylidene-2,5-cyclohexadien-one 252 g (0.4 mol) of bis-[3,5-di-tert.-butyl-4-hydroxy-($\alpha$-cyclohexen-$\Delta^3$-yl)-benzyl]sulphide, 1,000 ml of xylene and 300 g of basic lead carbonate are heated to the boil for 12 hours using a water separator, whereupon 8 ml of water are separated off. After filtering off the inorganic constituents, the yellow xylene solution is evaporated to dryness in vacuo. A viscous, red-brown oil remains as the residue.

Yield: 207 g; corresponding to 86.7% of theory, boiling point 0.05 mbar/145° C.

EXAMPLE 3

Preparation of 2,6-di-tert.-butyl-4-benzylidene-2,5-cyclohexadien-one 311 g (0.5 mol) of bis-[3,5-di-tert.-butyl-4-hydroxy($\alpha$-phenyl)-benzyl]sulphide, 1,000 ml of xylene and 190 g of basic lead carbonate are heated to the boil for 10 hours using a water separator, whereupon 10 ml of water are separated off. After filtering off the inorganic constituents, the filtrate is evaporated to dryness in vacuo. On cooling, the residue crystallises to give a yellow crystal mass.

Yield: 272 g=92.5% of theory, yellow crystals, melting point 74° to 76° C., boiling point 0.1 mbar/147° C.

EXAMPLE 4

Preparation of a solution of 2,6-di-tert.-butyl-4-methylidene-2,5-cyclohexadien-one 47 g (0.1 mol) of bis-(3,5-di-tert.-butyl-4-hydroxybenzyl)sulphide, 300 ml of xylene and 40 g of basic lead carbonate are boiled under nitrogen for 6 hours using a water separator, whereupon 2 ml of water pass over. By filtering off the inorganic constituents, a yellow xylene solution of the 3,5-di-tert.-butyl-p-quinone methide is obtained.

The 4-methylidene compound prepared is only stable in dilute solution and is characterised by recording the NMR spectrum (bands at 3.18, 4.38 and 8.73 $\gamma$).

EXAMPLES 5-15

The Examples 5 to 15 are carried out according to the instructions of Example 1 in the presence of basic lead carbonate. The reaction parameters are given in Table 1.

Table 1

| Example No. | Starting material | End product | Yield [%] | Properties of the end product | |
|---|---|---|---|---|---|
| 5 | Bis-[3,5-di-tert.-butyl-4-hydroxy-($\alpha$-tert.-butyl)-benzyl]sulphide | 2,6-Di-tert.-butyl-4-($\beta,\beta$-dimethyl)-propylidene-2,5-cyclohexadien-one | 81 | yellow crystals | m.p. 40°–42° C. |
| 6 | Bis-[3,5-di-tert.-butyl-4-hydroxy-($\alpha$-cyclohexyl)-benzyl]sulphide | 2,6-Di-tert.-butyl-4-cyclohexyl-methylidene-2,5-cyclohexadien-one | 83 | yellow crystals | m.p. 42°–44° C. |
| 7 | Bis-[3,5-di-tert.-butyl-4-hydroxy-($\alpha$-p-diphenyl)-benzyl]sulphide | 2,6-Di-tert.-butyl-4-p-diphenyl-methylidene-2,5-cyclohexadien-one | 89 | yellow crystals | m.p. 135°–137° C. |
| 8 | Bis-[3,5-di-tert.-butyl-4-hydroxy-($\alpha$-o-chlorophenyl)-benzyl]sulphide | 2,6-Di-tert.-butyl-4-o-chloro-phenyl-methylidene-2,5-cyclohexadien-one | 91 | yellow crystals | m.p. 109°–111° C. |
| 9 | Bis-[3,5-di-tert.-butyl-4-hydroxy-($\alpha$-m-chlorophenyl)-benzyl]sulphide | 2,6-Di-tert.-butyl-4-m-chloro-phenyl-methylidene-2,5-cyclohexadien-one | 97 | viscous red oil | b.p. 150° C./ 0.1 mbar |
| 10 | Bis-[3,5-di-tert.-butyl-4-hydroxy-($\alpha$-p-chlorophenyl)-benzyl]sulphide | 2,6-Di-tert.-butyl-4-p-chloro-phenyl-methylidene-2,5-cyclohexadien-one | 96 | yellow crystals | m.p. 132°–134° C. |
| 11 | Bis-[3,5-di-tert.-butyl-4-hydroxy-($\alpha$-o,p-dichlorophenyl)-benzyl]sulphide | 2,6-Di-tert.-butyl-4-o,p-dichloro-phenyl-methylidene-2,5-cyclohexadien-one | 83 | yellow crystals | m.p. 163°–165° C. |
| 12 | Bis-[3,5-di-tert.-butyl-4-hydroxy-($\alpha$-o,o-dichlorophenyl)-benzyl]sulphide | 2,6-Di-tert.-butyl-4-o,o-dichloro-phenyl-methylidene-2,5-cyclohexadien-one | 92 | yellow crystals | m.p. 112°–114° C. |
| 13 | Bis-[3,5-di-tert.-butyl-4-hydroxy-($\alpha$-o-tolyl)-benzyl]sulphide | 2,6-Di-tert.-butyl-4-o-tolyl-methylidene-2,5-cyclohexadien-one | 90 | yellow crystals | m.p. 99°–102° C. |
| 14 | Bis-[3,5-di-tert.-butyl-4-hydroxy-($\alpha$-m-tolyl)-benzyl]sulphide | 2,6-Di-tert.-butyl-4-m-tolyl-methylidene-2,5-cyclohexadien-one | 98 | yellow crystals | m.p. 55°–57° C. |
| 15 | Bis-[3,5-di-tert.-butyl-4-hydroxy-($\alpha$-p-tolyl)-benzyl]sulphide | 2,6-Di-tert.-butyl-4-p-tolyl-methylidene-2,5-cyclohexadien-one | 91 | yellow crystals | m.p. 143° C. |

EXAMPLE 16

55.4 g (0.1 mol) of bis-[3,5-di-tert.-butyl-4-hydroxy($\alpha$-isopropyl)-benzyl]sulphide, 300 ml of xylene and 40 g of lead-II oxide are heated to the boil for 10 hours using a water separator, whereupon about 2 ml of water are separated off. The organic constituents are filtered off from the xylene solution and the filtrate is concentrated to dryness in vacuo. On cooling; the residue crystallises to give a yellow crystal mass.

Yield: 22.8 g=44% of theory, yellow crystals, melting point 62° C.

EXAMPLE 17

63 g (0.1 mol) of bis-[3,5-di-tert.-butyl-4-hydroxy-($\alpha$-cyclohexen-$\Delta^3$-yl)-benzyl]sulphide, 300 ml of xylene and 67 g (0.3 mol) of lead-II oxide were heated to the boil for 25 hours using a water separator, whereupon about 2 ml of water are separated off. After filtering and evaporating the filtrate, an oil remains.

Yield: 44 g=74% of theory, viscous brown oil, boiling point 0.05 mbar/140°-150° C.

EXAMPLE 18

63 g (0.1 mol) of bis-[3,5-di-tert.-butyl-4-hydroxy-(α-cyclohexen-Δ³-yl)-benzyl]sulphide, 300 ml of dioxane and 67 g (0.3 mol) of lead-II oxide are heated under reflux for 25 hours. After filtering and evaporating the filtrate, an oil remains.

Yield: 21 g=36.5% of theory, viscous brown oil, boiling point 0.06 mbar/138°-148° C.

EXAMPLE 19

62.3 g (0.1 mol) of bis-[3,5-di-tert.-butyl-4-hydroxy-(α-phenyl)-benzyl]sulphide, 300 ml of xylene and 67 g (0.3 mol) of lead-II oxide are heated to the boil for 10 hours using a water separator, whereupon about 2 ml of water are separated off. After filtering and evaporating the filtrate, the residue crystallises out.

Yield: 41 g=70% of theory, yellow crystals, melting point 73°-75° C.

EXAMPLE 20

The procedure followed is as in Example 19, but 65 g of mercury-II oxide are used instead of lead-II oxide.

Yield: 41 g=70% of theory, yellow crystals, melting point 73°-75° C.

EXAMPLE 21

If a normal reflux condenser is used instead of a water separator in Example 3, a red oil is obtained under otherwise identical conditions, which only solidifies after standing for a relatively long time. After distillation at boiling point 0.09/140°-150° C., the same product is obtained from this in a yield of 72% of theory.

EXAMPLE 22

The procedure followed is as in Example 3, but toluene is employed as the solvent instead of xylene. The mixture is heated to the boil until 10 ml of water have been separated off. The yield is the same as in Example 3.

EXAMPLE 23

The procedure followed is as in Example 3, but benzene is employed as the solvent instead of xylene. The mixture is heated to the boil until 10 ml of water have been separated off. The yield is the same as in Example 3.

What is claimed is:

1. A process for preparing a 2,6-di-tert.-alkyl-4-alkylidene-2,5-cyclohexadien-one which comprises contacting at a temperature in the range of from 50° to 200° C. a bis-(3,5-di-tert.-alkyl-4-hydroxybenzyl)sulphide of the formula

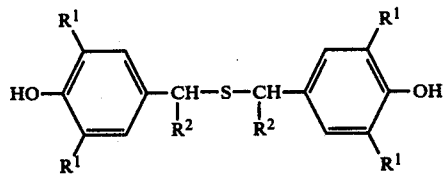

wherein
$R^1$ denotes a tertiary alkyl group and
$R^2$ denotes hydrogen, a straight or branched alkyl, cycloalkyl, cycloalkanyl, aralkyl or aryl group with lead or mercury in the oxide, hydroxide, carbonate, acetate or other basic reacting salt form in an inert solvent.

2. A process according to claim 1 wherein lead in the said form is employed.

3. A process according to claim 2 wherein basic lead carbonate is employed.

4. A process according to claim 1 wherein mercury in the said form is employed.

5. A process according to claim 1 wherein an excess of lead or mercury in the said form is employed.

6. A process according to claim 1 wherein the reaction is carried out in boiling xylene and water formed during the reaction is simultaneously removed by azeotropic distillation.

* * * * *